United States Patent [19]
Brown et al.

[11] Patent Number: 6,142,984
[45] Date of Patent: *Nov. 7, 2000

[54] REMOVAL STRING FOR TAMPON PLEDGET

[75] Inventors: Jeffrey M. Brown, Ramsey; Dane R. Jackson, Bloomingdale; Suzanne M. Pauley, Hackensack, all of N.J.

[73] Assignee: Playtex Products, Inc., Westport, Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/000,735

[22] Filed: Dec. 30, 1997

[51] Int. Cl.⁷ .................................................. A61F 13/20
[52] U.S. Cl. .................... 604/385.18; 604/904; 427/387; 427/389.9
[58] Field of Search ................................. 422/387, 389.9; 604/385.6, 387, 378, 381, 384, 904, 385.17, 385.18

[56] References Cited

U.S. PATENT DOCUMENTS

| | | |
|---|---|---|
| Re. 28,674 | 1/1976 | Guyette . |
| 2,024,218 | 12/1935 | Haas . |
| 2,146,985 | 2/1939 | Rabell . |
| 2,519,912 | 8/1950 | Laun . |
| 3,037,506 | 6/1962 | Penksa . |
| 3,102,541 | 9/1963 | Adams . |
| 3,204,635 | 9/1965 | Voss et al. . |
| 3,452,752 | 7/1969 | De Crescenzo . |
| 3,520,302 | 7/1970 | Jones . |
| 3,625,787 | 12/1971 | Radl et al. . |
| 3,794,024 | 2/1974 | Kokx et al. . |
| 3,857,395 | 12/1974 | Johnson et al. . |
| 3,948,257 | 4/1976 | Bossak . |
| 3,999,549 | 12/1976 | Poncy et al. . |
| 4,230,686 | 10/1980 | Schopflin et al. ........................ 424/22 |
| 4,332,251 | 6/1982 | Thompson . |
| 4,743,237 | 5/1988 | Sweere . |
| 4,755,166 | 7/1988 | Olmstead . |
| 5,203,767 | 4/1993 | Cloyd . |
| 5,429,628 | 7/1995 | Trinh et al. . |
| 5,458,589 | 10/1995 | Comin-DuMong . |
| 5,478,335 | 12/1995 | Colbert .................................... 604/383 |
| 5,533,990 | 7/1996 | Yeo . |
| 5,618,281 | 4/1997 | Betrabet et al. ........................ 604/387 |
| 5,891,126 | 4/1999 | Osborn, III et al. ................ 604/385.1 |

*Primary Examiner*—Brian K. Talbot
*Attorney, Agent, or Firm*—Ohlandt, Greeley, Ruggiero & Perle, LLP

[57] ABSTRACT

A tampon including a pledget with a textured tampon string. The string is one or more of the following constructions: crocheted, cabled, braided or a combination of two or more thereof. The textured tampon string may have a siloxane solution applied thereto or included therein.

20 Claims, No Drawings

REMOVAL STRING FOR TAMPON PLEDGET

The present invention is directed to a tampon string. More particularly, the present invention is directed to a tampon string that has a textured exterior surface. The textured exterior surface has varying thicknesses along its axial extent, and the variations in thickness occur at regular intervals. The textured tampon string especially with regular variations in thickness provides enhanced grippability and aesthetics. Moreover, the configuration of the textured tampon string increases the tensile strength of the string. Furthermore, the textured tampon string has, unexpectedly, been found to accept certain coatings that provide the string with a non-wicking ability.

BACKGROUND OF THE INVENTION

A tampon is provided with a string to facilitate removal of a tampon after use. The string is normally made of a single ply or multiple plies of yarn. Heretofore, the selection of the string has been a balance of two competing concerns. The first concern was that the string have a sufficiently large diameter as to be grippable by the user, and that the string withstand the pull force applied to remove the tampon from the body. The second, competing concern was that the user does not want to notice or feel the string when the tampon is in place. Accordingly, this second concern has normally been addressed by using a thinner, lighter and, thus, less strong string. The balancing of these competing concerns has proven difficult in practice.

Thus, an improved tampon string is needed that provides enhanced grippability, has sufficient tensile strength, and yet is aesthetically acceptable to the user. Moreover, the improved tampon string should have an improved resistance to fluid wicking. This improved resistance to fluid wicking, also called the non-wicking ability of the string, further enhances the grippability of the string, as well as results in less or no staining of the user's undergarment.

SUMMARY OF THE INVENTION

Accordingly, it is an object of the present invention to provide a textured tampon string.

It is another object of the present invention to provide such a textured tampon string that improves or enhances the grippability of the tampon string.

It is still another object of the present invention to provide such a textured tampon string that unexpectedly is receptive to certain coatings so that the string is also substantially non-wicking and, thus, prevents the movement of fluids along the length of the tampon string.

It is yet another object of the present invention to provide such a textured tampon string that has tensile strength that is the same or greater than that of existing tampon strings.

It is still yet another object of the present invention to provide such a textured tampon string that is comfortable and virtually undetectable to the user when the tampon is being used, and is aesthetically pleasing.

It is a further object of the present invention to provide such a textured tampon string that is formed by crotcheting, cabling or braiding, preferably more than one strand of yarn.

It is still a further object of the present invention to provide such a textured tampon string in which the crotcheted, cabled or braided strands of yarn are in tight, substantially continuous contact with each other along the length of the tampon string.

It is yet still a further object of the present invention to provide such a textured tampon string that has varying diameters and/or cross-sections at regular intervals along the length of the tampon string.

It is still yet a further object of the present invention to provide such a textured tampon string that has less fiber and less weight than known tampon strings having the same tensile strength.

Accordingly, the present invention provides a textured tampon removal string connected to a tampon or pledget, or the coverstock of the pledget. The string can be a crocheted, cabled or braided string or a combination thereof in order to provide a textured outer or exterior surface having regular varying diameters and/or cross-sections. Also, the tensile strength of the textured tampon string is the same or better than existing tampon strings. The textured tampon string is preferably treated with a non-wicking coating.

In a preferred embodiment, the textured tampon string has a crotcheted configuration, and is composed of four strands of yarn. It is preferred that each strand of yarn is polyester.

DESCRIPTION OF THE PREFERRED EMBODIMENTS

The present invention relates to a textured tampon string. The textured tampon string is a string used to remove a tampon from the body. Presently, the most commonly available tampon strings are twisted strings. A twisted tampon string can be formed of multiple strands or plies of yarn for increased strength. These yarns are commonly twisted in a single axis to form a simple twisted tampon string.

The textured tampon string has one or more strands of yarn. Each strand of yarn has one or more filaments. Preferably, the textured string has more than one strand of yarn. The textured string has one of the following configurations, namely crocheted, cabled or braided or a combination of two or more thereof. In the more preferred embodiments, the string is either crocheted or cabled. In the most preferred embodiment, the string is crocheted.

In the textured configurations, the individual strands of yarn in the multi-strand (more than one strand) textured tampon string remain in substantially continuous contact with one another along the entire extant or length of the tampon string. Also, the textured string of the present invention is thicker than an uncrocheted string of the same number of strands and type of yarn.

As compared to the commonly available simple twisted tampon string that is formed of multiple strands of yarn, the textured string has approximately the same average circumference or diameter. However, the textured tampon string has a more pronounced variation in diameter (and circumference) along its axial extant or length than the simple twisted tampon string. For example, the present textured tampon string has a more pronounced variation in diameters and/or cross-sections along its length, whereas the simple twisted tampon string has a more uniform diameter and cross-section along its length. The variations in diameter and cross-section along the length of the textured tampon string provides an enhanced texturing or outer surface and, thus, enhanced grippability of the string. Further, the variations in diameter or cross-section occur at more regular intervals along the axial extant of the textured string. This feature will further enhance the ability of one to grasp the string anywhere along its axial extent and still have improved grippability.

It is preferred that the present textured tampon string be constructed with a sufficiently, tight crochet. Such a tight crochet means that all strands of yarn remain in continuous contact with each other under normal conditions. This tighter contact provides a more stable and grippable string. The tighter contact or stitch is pearl-like, with discrete surface areas that improve grippability, as well as providing a more aesthetically pleasing appearance and feel.

Significantly, loose contact or stitches have greater elasticity that will facilitate elongation or distortion of the tampon string. Such elongation or distortion causes difficulty for the user during tampon removal. Accordingly, such looser stitches result in less removal confidence. Thus, the tight crotcheting of the present textured tampon string enhances removal confidence and, thus, overall acceptability of the tampon.

Another benefit of the present textured tampon string is that it provides the same or improved tensile strength without excess weight. Tensile strength is a resistance to elongation or axial pulling of the tampon string. Known tampon strings have typically added fiber (and consequently added weight) to the string to increase its tensile or pull apart strength.

The formation techniques, such as tight, continuous contact of the strands of yarn, of the present textured tampon string increases its tensile strength, and may increase its bulk, without increasing the amount of fiber or the weight of the tampon string. The formation techniques of the present invention allow the form of the string itself to be changed so that this tampon string, with the same weight per unit length as a commonly known tampon string, has increased tensile strength. It is believed that this increased tensile strength over known tampon strings is, as discussed above, due to the linkage or substantially continuous contact of all strands of yarn of the tampon string. This linkage or continuous contact results from the crochet, cable, braid or a combination of two or more thereof configurations of the present textured tampon string.

As stated above, in the most preferred embodiment of the textured tampon string of the present invention, the string is a crocheted or crocheted knitted tampon string. The crocheted string is a string made by interlocking a series of loops with one or more strands of yarn.

The second preferred textured string is a cabled string. A cabled string formed by cabling, which is a process suitable for mass production, is made from an assembly of individual strands laid up together by being twisted around a separate strand of yarn referred to as the core.

The third of the three textured string embodiments is a braided string. A braided string means a string made by interwining two or more strands of yarn to make a cord. The strands form a regular diagonal pattern down the length of the cord. See also *Wellington Sears Handbook of Industrial Textiles* by Sabit Adanur, published by Technomic Publishing Co., Inc., 1995, which is incorporated herein by reference.

The textured tampon string is preferably attached directly to the tampon or pledget, or the coverstock of the pledget, by methods known in the art. Also, the textured tampon string is preferably knotted at its opposite or free end.

A single texturing technique is preferred for use. In addition, it is preferred economically that the textured string of the present invention be formed by a single texturing technique or method. However, more than one texturing technique can be used, and a combination of two or more methods or techniques can be used. For example, it is believed that for cabling and braiding, and perhaps crotcheting, in which the textured string is made of two or more strands of yarn, one may first texture the two individual strands of yarn and subsequently using the same texturing techique (crotcheting, cabling or braiding) texture the two or more strands of yarn together. Alternatively, one may simply texture the two or more strands of yarn that have already been joined together.

The filaments of the strands of yarn of the textured tampon string are preferably made of polyester, polypropylene, polyethylene, rayon or a combination thereof. Most preferably, the filaments are made of polyester. Such polyester filaments are bundled into strands, most preferably 50 filaments per strand resulting in 240 denier per strand of yarn.

These strands of yarn are then crocheted, cabled or braided into a finished string. Most preferably, a finished textured tampon string has four strands of yarn. In crocheting, the most preferred textured string has four strands which are woven together at the interval of 10 pics/inch. Thus, each loop is about one-tenth of an inch long. The finished textured tampon string is about 960 denier (240 denier×4 ends). A textured tampon string that is substantially less than about 1000 denier is not as grippable as a textured tampon string that is near or greater than about 1000 denier. Thus, the textured tampon string should not be less than 700 to 800 denier.

In addition to being grippable, the textured tampon string is preferably non-wicking since a non-wicking string will not transmit fluids along its length. Thus, a non-wicking string functions better sin(e a wet or wicking string is less grippable. Also, a non-wicking string minimizes the likelihood that menstrual fluids will stain a user's undergarment. It is preferred that the textured tampon string of the present invention be treated or fabricated to be substantially non-wicking.

It has unexpectedly been found that the preferred polyester crotcheted textured tampon string can be made non-wicking by the application of a particular coating. Polyester by its nature is repellent, but it becomes wicking once formed into a crocheted string. However, unexpectedly the crocheted polyester string is receptive to siloxane coating, the preferred non-wicking coating of the present invention.

The non-wicking treatment or coating of the textured tampon string can be achieved in one of two basic methods. In one method, the formed textured tampon string is treated. In the second method, the individual strands of yarn are treated and, thereafter, the finished textured tampon string is formed. Apparently, the non-wicking treatment can also be achieved by a combination of the above two methods.

There is a preferred non-wicking solution or coating that can be applied or coated to preferably either the strands of yarn prior to crocheting, cabling or braiding, or applied to the finished textured tampon string, to minimize or eliminate the wicking capacity of the string.

The solution is applied by one of the processes known in the art. Most preferably, the solution is applied by a common commercial padding process and then cured and dried. This padding process includes dipping the string or strand of yarn (possibly just the filament) in fluid and passing the string or strand of yarn through rollers to squeeze out excess fluid. Heat is applied to start drying the strand of yarn or string and to expedite the cross-linking that occurs in the solution. More preferably, the solution is applied as an emulsion in a range about 2% to about 5% solids solution with a wet pickup of about 40 to about 75 percent by weight. After the emulsion is applied, the string is cured. A preferred curing is to heat the string to about 275 degrees F to about 350 degrees F for about one to about seven minutes. Alternatively, the emulsion can be applied, dried and after winding (strand or string can be wound including onto a spool) can be cured on the finished spool.

The non-wicking coating or solution used in the present invention is siloxane. More preferably, the solution is an organomodified siloxane. This solution has less than about 50 percent by weight of water, more than about 40 percent by weight of amino polysiloxane, and less than about 10 percent by weight of a proprietary additive.

Siloxanes will not adhere to many substrates. Thus, it is surprising that siloxane adheres to the polyester strands of the preferred textured string. Moreover, it has surprisingly been found that the siloxane coating, which is normally slippery, appears to go into the interstices of the textured tampon string. Consequently, the tampon string's surface is not made slippery by the coating so that the grippability of the string is not undermined.

Other hydrophobic treatments may also be applied successfully to the textured tampon string of the present invention. Moreover, it has unexpectedly been discovered that a synergistic relationship exists between the textured tampon string of the present invention and the non-wicking treatment. The preferred polyester fibers are damaged somewhat by the texturing process (e.g., crocheting, cabling or braiding). This damage is corrected and compensated for by the application of the non-wicking treatment. Apparently, any microscopic fiber tears are compensated for by the cured non-wicking treatment.

Tests performed on treated and untreated strings demonstrate the anti-wicking properties of the organosiloxane coated string. Three foot-long lengths of string were tested for wicking. The first string was treated with a bath solution of 4 weight percent organomodified siloxane solution and 96 weight percent distilled water. The second string was treated with distilled water. The third string was left untreated. The treated strings were allowed to dry and cure for five minutes at 130° C. (266° F.). The lower ends of the strings were then placed in a 0.01% methylene blue colored solution bath, and the height of the stain rise was measured after four hours of partial immersion. The solution treated string showed a 23 mm stain above the surface of the solution. The water treated string showed a 130 mm stain, or more than a fivefold increase in wicking. The untreated string showed a 105 mm stain, a fourfold increase in wicking versus the solution treated string.

Tampons having textured tampon strings, both with or without the preferred non-wicking coating, demonstrate substantially improved performance in comparison with the conventional tampons.

In one test, 100 respondents compared tampons having (1) a siloxane coated, crocheted unknotted string, and (2) a conventional unknotted, coated twisted cotton string were tested. The coating on the cotton string is a typical water repellent coating, such a NALAN made by E. I. du Pont de Nemours & Co., Inc. It is a durable water repellent of the polymer-wax dispersion family and has less than 6% acetic acid. This coating does not uniformly adhere to polyester. The reasons for the preference of the respondents are listed below. Only those respondents who preferred one tampon over another are shown. The remainder of the 100 respondents indicated no preference.

| Reason for Preference | # Preferring Crocheted | # Preferring Untextured |
| --- | --- | --- |
| Thickness | 45 | 30 |
| Being easy to find | 38 | 28 |
| Not leaking down string | 37 | 29 |
| Secure string | 38 | 21 |
| Being easy to grip | 46 | 22 |
| Good removal string | 43 | 21 |

The test demonstrated a marked preference for the coated, textured string made by crocheting. It is also believed that this preferred crotcheted string could have even further enhanced grippability properties by the use of a knot at the free end or ends of the string.

A second test was performed comparing the non-wicking properties of the siloxane coated, crotcheted textured string, a cotton string coated with NALAN and a string used on a present Tambrands Tampax tampon. The cotton string is made via spinning and/or twisting cotton fibers into a continuous strand. The Tampax string is made via sewing a separate thread along the length of a conventional twisted cotton string. The test involved immersing the end of the sample strings into blue dyed saline solution and noting over time the wicking of the dye up each string.

| String | Distance Wicked (millimeters/hour) |
| --- | --- |
| Crocheted | repels fluid |
| Tampax | 1–2 |
| Cotton | 1–2 |

Thus, it will be obvious to one of ordinary skill in the art that the foregoing description is merely illustrative of certain preferred embodiments of the present invention, and that various obvious modifications can be made to these embodiments in accordance with the spirit and scope of the appended claims.

What is claimed is:

1. A tampon comprising:
   a pledget;
   a textured tampon string connected to said pledget, said string being selected from the group of constructions consisting of crotcheted, cabled, braided, and combinations of two or more thereof; and
   a non-wicking coating on said textured tampon string, said coating comprising a siloxane which decreases wicking of a fluid along the string.

2. A tampon of claim 1, wherein the string is made of a material selected from the group consisting of: polyester, polypropylene, polyethylene, rayon, and combinations thereof.

3. A tampon of claim 1, wherein the siloxane comprises an organomodified polysiloxane.

4. A string for a tampon pledget, the string being coated with a solution comprising siloxane, wherein the string demonstrates a decreased wicking of a fluid along the string.

5. The string of claim 4, wherein the string comprises at least two strings.

6. The string of claim 4, wherein the string is a textured tampon string having a construction selected from the group consisting of crotcheted, cabled, braided, and combinations thereof.

7. The string of claim 4, wherein the string is made of a material selected from the group consisting of: polyester, polypropylene, polyethylene, rayon, and combinations thereof.

8. The string of claim 4, wherein the siloxane comprises an organomodified polysiloxane.

9. The string of claim 4, further comprising a coverstock about the tampon pledget, and wherein the string is connected to the coverstock.

10. A method of substantially improving the performance of a string of a tampon pledget comprising applying a solution comprising siloxane to the string, wherein the improved performance is decreased wicking of a fluid along the string.

11. The method of claim 10, further comprising the step of curing the siloxane solution.

12. The method of claim 10, wherein the siloxane includes an organomodified polysiloxane.

13. The method of claim 10, wherein the string comprises at least two strings.

14. The method of claim 10, further comprising forming a textured tampon string from the at least two removal strings, the textured tampon string having a construction selected from the group consisting of: crotcheted, cabled, braided, and combinations thereof.

15. The method of claim 14, wherein forming the textured tampon string is prior to applying the solution to the textured tampon string.

16. The method of claim 14, wherein applying the solution to the at least two strings is prior to the forming of the textured tampon string.

17. The method of claim 15, wherein the at least two removal strings is four strings.

18. The method of claim 15, wherein the substantial improvement in performance further comprises enhanced grippability of the removal string.

19. The method of claim 10, wherein the string is made of a material selected from the group consisting of: polyester, polypropylene, polyethylene, rayon, and combinations thereof.

20. The method of claim 14, wherein the textured tampon string is made of a material selected from the group consisting of: polyester, polypropylene, polyethylene, rayon, and combinations thereof.

* * * * *